(12) United States Patent
Jain et al.

(10) Patent No.: US 9,482,608 B1
(45) Date of Patent: Nov. 1, 2016

(54) WGM-BASED MOLECULAR SENSORS

(71) Applicants: Ravinder Jain, Albuquerque, NM (US); Mani Hossein-Zadeh, Albuquerque, NM (US)

(72) Inventors: Ravinder Jain, Albuquerque, NM (US); Mani Hossein-Zadeh, Albuquerque, NM (US)

(73) Assignee: STC.UNM, Albuquerque, NM (US)

( * ) Notice: Subject to any disclaimer, the term of this patent is extended or adjusted under 35 U.S.C. 154(b) by 0 days.

(21) Appl. No.: 14/659,579

(22) Filed: Mar. 16, 2015

Related U.S. Application Data

(60) Provisional application No. 61/953,891, filed on Mar. 16, 2014.

(51) Int. Cl.
*G01J 5/02* (2006.01)
*G01N 21/3504* (2014.01)
*G01N 21/27* (2006.01)

(52) U.S. Cl.
CPC .......... *G01N 21/3504* (2013.01); *G01N 21/27* (2013.01); *G01N 2201/0686* (2013.01); *G01N 2201/06113* (2013.01)

(58) Field of Classification Search
CPC ............. G01N 2021/399; G01N 2021/06113; G01N 2201/067; G01N 2201/0686; G01N 21/3504; G01N 21/27
USPC .................................................... 250/339.01
See application file for complete search history.

(56) References Cited

U.S. PATENT DOCUMENTS

| | | | | |
|---|---|---|---|---|
| 8,149,407 B1* | 4/2012 | Rao | ......... | G02B 5/003 356/437 |
| 8,399,837 B2* | 3/2013 | Robbins | ......... | A61B 5/083 250/339.13 |
| 9,140,606 B2* | 9/2015 | Witinski | ......... | G01J 3/433 |
| 2003/0189711 A1* | 10/2003 | Orr | ......... | G01J 3/42 356/484 |
| 2004/0150818 A1* | 8/2004 | Armstrong | ......... | B82Y 10/00 356/301 |
| 2007/0064748 A1* | 3/2007 | Mirov | ......... | C30B 31/00 372/20 |
| 2007/0252995 A1* | 11/2007 | Shaw | ......... | G01N 21/552 356/437 |
| 2008/0285606 A1* | 11/2008 | Kippenberg | ......... | G02F 1/39 372/32 |
| 2009/0263137 A1* | 10/2009 | Hossein-Zadeh | ......... | H04B 1/30 398/115 |
| 2011/0058248 A1* | 3/2011 | Vodopyanov | ......... | G02F 1/39 359/330 |
| 2011/0267603 A1* | 11/2011 | Shaw | ......... | G01N 21/431 356/128 |
| 2012/0300209 A1* | 11/2012 | Witinski | ......... | G01N 21/3504 356/409 |
| 2013/0156051 A1* | 6/2013 | Peccianti | ......... | H01S 3/06712 372/18 |
| 2014/0290311 A1* | 10/2014 | Jain | ......... | G02B 6/02052 65/441 |

* cited by examiner

*Primary Examiner* — David J Makiya
*Assistant Examiner* — Taeho Jo
(74) *Attorney, Agent, or Firm* — Keith A. Vogt; Vogt IP

(57) ABSTRACT

The present invention concerns an optical molecular sensing device and related method. The optical molecular sensing device has an optical resonator adapted to be connected to an excitation source. The excitation source may be a laser operating at a 2.7-2.8 um spectral range. The optical molecular sensing device has an emission spectrum comprised of a plurality wavelengths. Also included are a detection unit and a RF frequency counter to detect at least one RF beat note resulting from detecting the emission spectrum of the optical resonator. A change in frequency of the RF beat note indicates the presence of a target molecule.

19 Claims, 14 Drawing Sheets

Partial energy level diagram of the Er$^{+3}$ ion. ETU1 and ETU2 designate energy transfer upconversion processes (ETU1 rate > ETU2 rate) that become important at high pump intensities and small inter-ion separation (high doping densities).

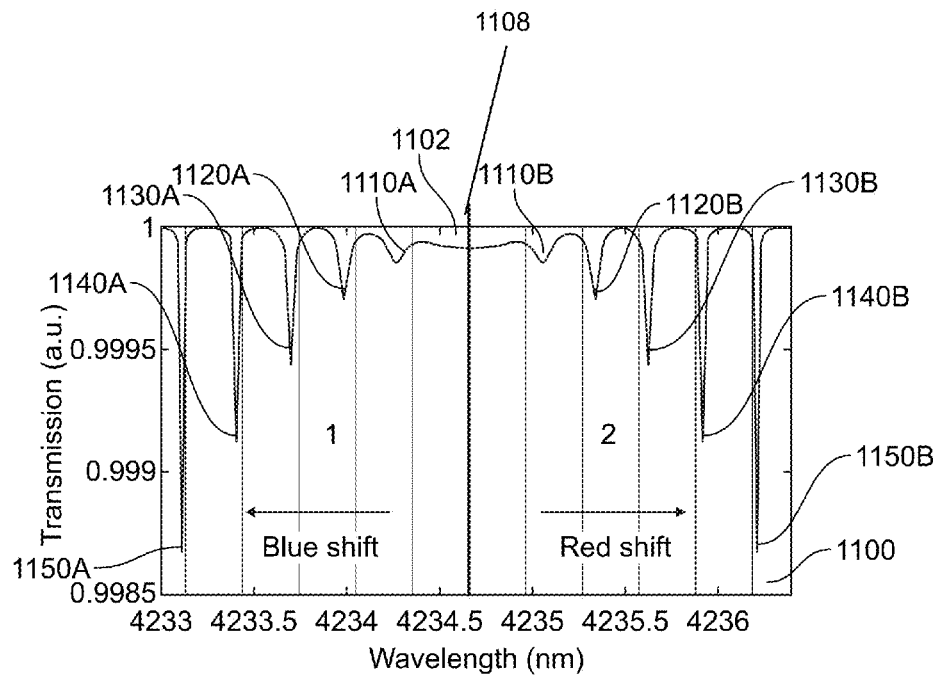

Transmission spectra of microresonator (with an intrinsic quality factor of $10^6$) in vacuum (red curves) and in presence of $CO_2$ molecules at one atmosphere pressure (blue curves).

FIG. 11

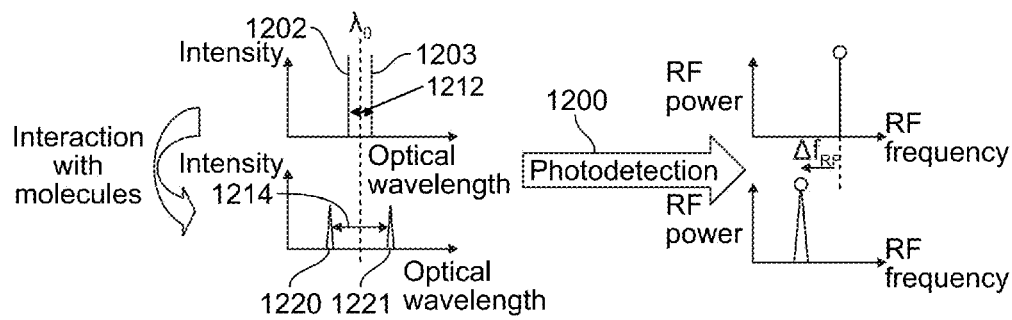

The optical (Fig. 12A) and RF (Fig. 12B) spectra of the emission from high-Q resonant source that has two lines within the molecular absorption bandwidth, before and after interaction with molecules.

FIG. 12

WGM-BASED MOLECULAR SENSORS

RELATED APPLICATIONS

This application claims the benefit of U.S. Provisional Application No. 61/953,891, filed Mar. 16, 2014 and herein incorporated by reference.

STATEMENT REGARDING FEDERALLY SPONSORED RESEARCH & DEVELOPMENT

This invention was made with government support under United States Air Force Office of Scientific Research grant FA9550-12-1-0049 and National Science Foundation grant ECCS-1232263. The government has certain rights in the invention.

INCORPORATION BY REFERENCE OF MATERIAL SUBMITTED ON A COMPACT DISC

Not applicable.

BACKGROUND OF THE INVENTION

High optical quality (high-Q) whispering gallery mode (WGM) microresonators have been a subject of intense investigation during the last decade because of their strong potential for numerous high-performance photonic devices, including ultra-sensitive molecular detectors and advanced light sources, such as narrow linewidth lasers and comb generators. The unique characteristics of such WGM devices appear to be particularly relevant for mid-infrared (MIR) applications, because of the stronger molecular absorption lines in the MIR, and because of the increasing need for frequency comb sources in this "molecular fingerprint" region. In particular, prior efforts have estimated a sensitivity of a few parts per trillion for the detection of several strongly-absorbing atmospheric and biogenic trace gases in this MIR "molecular fingerprint" region by combining the sensitivity benefits of wavelength modulation spectroscopy with high-Q MIR microsensors in compact "field-usable devices", facilitating their use for numerous applications in industry, environmental sensing, and agriculture. Such miniature portable "ultra-sensitive" molecular sensors could pave the way for numerous cutting-edge uses in diverse fields and applications such as: (1) breath analysis of patients for healthcare; (2) process control systems (such as ultrasensitive moisture monitoring) in manufacturing; (3) environmental monitoring of industrial pollutants, including hydrogen sulphide and carbon monoxide levels (say on roadsides and in parking structures); (4) the precise monitoring of trace gases that affect the environment, such as $CO_2$ and other greenhouse gases, biogenic emissions from flora and fauna, coastal and oceanic carbon and nitrogen compounds, and geothermal and volcanic emissions; and (5) measurements of emissions from agricultural enterprises including crop growth and livestock farming (e.g., ammonia emissions).

There have also been considerable advances in the development of Whispering-Gallery mode (WGM) microlasers in the past decade as key enablers for numerous high-performance photonic devices, including ultrasensitive molecular detectors and compact narrow-linewidth lasers. Most of the past WGM microlaser developments have focused on visible and near-IR sources.

Whispering-gallery-mode (WGM) microlasers are particularly attractive and popular, largely because of their relative ease of fabrication (as opposed to their electrically pumped semiconductor counterparts, which require much more elaborate design and fabrication processes. Even though optically pumped microlasers have been demonstrated with a broad range of glass and crystal hosts, spherical and toroidal structures, based on the rare-earth-doped silica material system, are the most common, in part, because of the ease of fabrication of such structures via simple melting techniques.

Unfortunately, silica-based microlasers are limited in their operating wavelength ranges to the visible and near-IR because of the strong increase in absorption in silica at wavelengths >2 µm. However, because of the stronger molecular absorption bands in the mid-infrared (MIR), ultra compact, microlaser sources at longer MIR wavelengths are still critically needed for several key applications, notably high-resolution spectroscopy and trace level detection of several important molecular species. Previous mid-IR WGM microlasers have been based on electrically pumped semiconductor sources that are difficult to fabricate and are also limited to operation either at cryogenic temperatures, or in the pulsed mode at relatively short (2.4 µm) MIR wavelengths.

BRIEF SUMMARY OF THE INVENTION

In one embodiment, the present invention exploits the strong dispersion of resonant modes near molecular absorption lines, and reduces the cost and complexity of molecular sensors by eliminating the need for tunable lasers; moreover, the detection speed of the present invention is much faster, and limited only by the cavity buildup time (typically of the order of nanoseconds or less), enabling "real time" monitoring. In addition, other embodiments of the microlaser of the present invention are not based on electrically-pumped semiconductor sources or require cryogenic temperatures to operate. Embodiments of the present invention are able to operate in temperature from 32 degrees below zero and higher.

In other embodiments, the present invention provides a room temperature MIR WGM microlaser operating in the 2.7-2.8 um spectral range where there are a plethora of molecular absorption lines. This embodiment was achieved by fabricating high-Q erbium-doped ZBLAN microspheres and optically pumping such Er:ZBLAN microspheres with a 980 nm diode laser. Using elevated erbium concentrations enables mid-IR WGM laser generation.

In another embodiment, the present invention provides a continuous-wave (cw) room temperature (RT) mid-IR WGM microlaser system capable of operating at a spectral range (2.7-2.8 µm) that overlaps strong transitions of several molecular species of significant interest for sensing applications. Applications for the embodiments of the present invention include, but are not limited to, detection at trace levels for: (1) environmental sensing ($NO_2$, $CO_2$, $CO$, $H_2S$, and $AsH_3$), (2) industrial process monitoring (trace water vapor levels for semiconductor fab and fiber preform manufacturing), and (3) health care (including breath analysis). In one embodiment, the cw MIR microlasers may be achieved by optically pumping high-Q WGM spherical erbium-doped fluoride glass microresonators with a low-power 980 nm diode laser.

BRIEF DESCRIPTION OF THE SEVERAL VIEWS OF THE DRAWINGS

In the drawings, which are not necessarily drawn to scale, like numerals may describe substantially similar components throughout the several views. Like numerals having different letter suffixes may represent different instances of substantially similar components. The drawings illustrate generally, by way of example, but not by way of limitation, a detailed description of certain embodiments discussed in the present document.

FIG. 2a is a schematic diagram of an MIR microsphere laser for one embodiment of the present invention.

FIG. 2b is a micrograph of Er:ZBLAN microspheres of ~180 μm diameter before optimized optical pumping of the embodiment shown in FIG. 2a.

FIG. 2c is a micrograph of Er:ZBLAN microspheres of ~180 μm diameter during optimized optical pumping of the embodiment shown in FIG. 2a.

FIG. 11 shows a transmission spectra of microresonator (with an intrinsic quality factor of $10^8$) in vacuum (curves 1100) and in presence of $CO_2$ molecules at one atmosphere pressure (curves 1102).

FIG. 12 shows the optical (a) and RF (b) spectra of the emission from high-Q resonant source that has two lines within the molecular absorption bandwidth, before and after interaction with molecules.

DETAILED DESCRIPTION OF THE INVENTION

Detailed embodiments of the present invention are disclosed herein; however, it is to be understood that the disclosed embodiments are merely exemplary of the invention, which may be embodied in various forms. Therefore, specific structural and functional details disclosed herein are not to be interpreted as limiting, but merely as a representative basis for teaching one skilled in the art to variously employ the present invention in virtually any appropriately detailed method, structure or system. Further, the terms and phrases used herein are not intended to be limiting, but rather to provide an understandable description of the invention.

In the formation of microlasers, glasses are particularly attractive as host media because of the relative ease of shaping and "processing" glass hosts into high-Q resonators via relatively simple polishing and melting techniques. However, the relatively robust and popular silicate glasses are precluded from use at MIR laser wavelengths >2 µm (because of their relatively high absorption at the longer wavelengths). Nevertheless, numerous fluoride, telluride, and chalcogenide glasses are attractive choices of glass hosts for MIR lasers because of their relatively high transparency, even at wavelengths >4 µm, provided they are "formable" into high-Q resonators and can also act as "good solvents" or solid-state hosts for sufficiently high doping densities of the appropriate rare-earth ions for the requisite gain at the desired MIR wavelengths.

A method of fabricating high-Q microspheres is disclosed in U.S. patent application Ser. No. 13/960,659, filed Aug. 6, 2013, the disclosure of which is herein incorporated by reference in its entirety. High-Q microspheres may be made from fluoride glasses including ZBLAN ($ZrF_4$—$BaF_2$—$LaF_3$—$AlF_3$—NaF), a fluoride glass characterized by relatively high glass stability, and with known high solubility for a large number of well-understood MIR rare-earth dopants, notably erbium, holmium, praesodymium, and dysprosium. As such, ZBLAN represents a suitable host glass for use in connection with one or more embodiments of the present invention.

Figure 1:
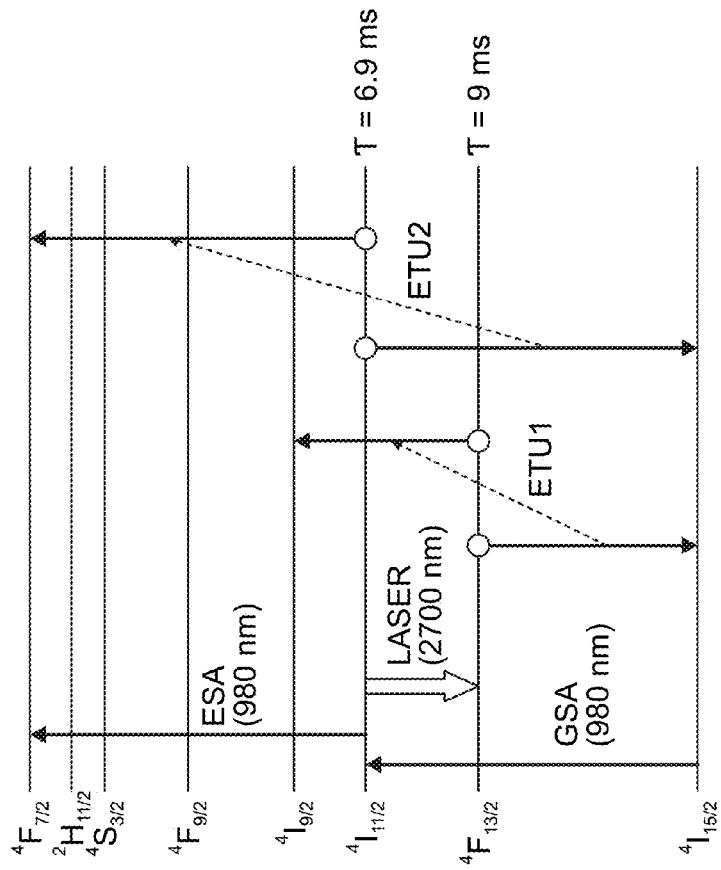
FIG. 1 shows a partial energy level diagram of the $Er^{+3}$ ion. ETU1 and ETU2 designate energy transfer upconversion processes (ETU1 rate>ETU2 rate) that become important at high pump intensities and small inter-ion separations (high doping densities).

In addition, embodiments of the present invention may use erbium (Er) as the gain ion. FIG. 1 shows, for an embodiment of the present invention, a partial energy level diagram of Er ions in ZBLAN. At very low erbium concentrations, where the interaction between erbium ions is negligible, the longer natural lifetime of the lower energy level of $^4I_{13/2}$ ($\tau_1$=9 ms) relative to that of the upper energy level of $^4I_{11/2}$ ($\tau_2$=6.9 ms) results in a population bottleneck that inhibits inversion and efficient steady state lasing between these two energy levels is obtained. As such, in all previously reported Er:ZBLAN (and Er:silica) WGM microlasers, the lasing action occurred solely due to inversion between the $^4I_{13/2}$ and $^4I_{15/2}$ states, resulting in lasing wavelengths near 1550 nm.

For some embodiments of the microlasers of the present invention, a maximum erbium ion solubility that is readily achievable (8 mol. %) to enhance the ETU1 cross-relaxation (CR) process via dipole-dipole energy transfer between closely spaced erbium ions that have been simultaneously excited to the $^4I_{13/2}$ state (via optical pumping) is provided. The higher doping densities and CR processes facilitate population inversion between the $^4I_{11/2}$ and $^4I_{13/2}$ levels to enable attainment of extremely high gains per unit length at this 2.7 µm transition, even with relatively low pump powers.

In other embodiments, microspheres were fabricated using uniformly doped (8 mol. %) Er:ZBLAN fibers of 100 µm diameter and no cladding, using a controlled symmetric heating process. It should be noted, however, that these doping densities are still too low to have significant effect on the thermal and crystallization properties of the Er:ZBLAN glass.

Figure 2:
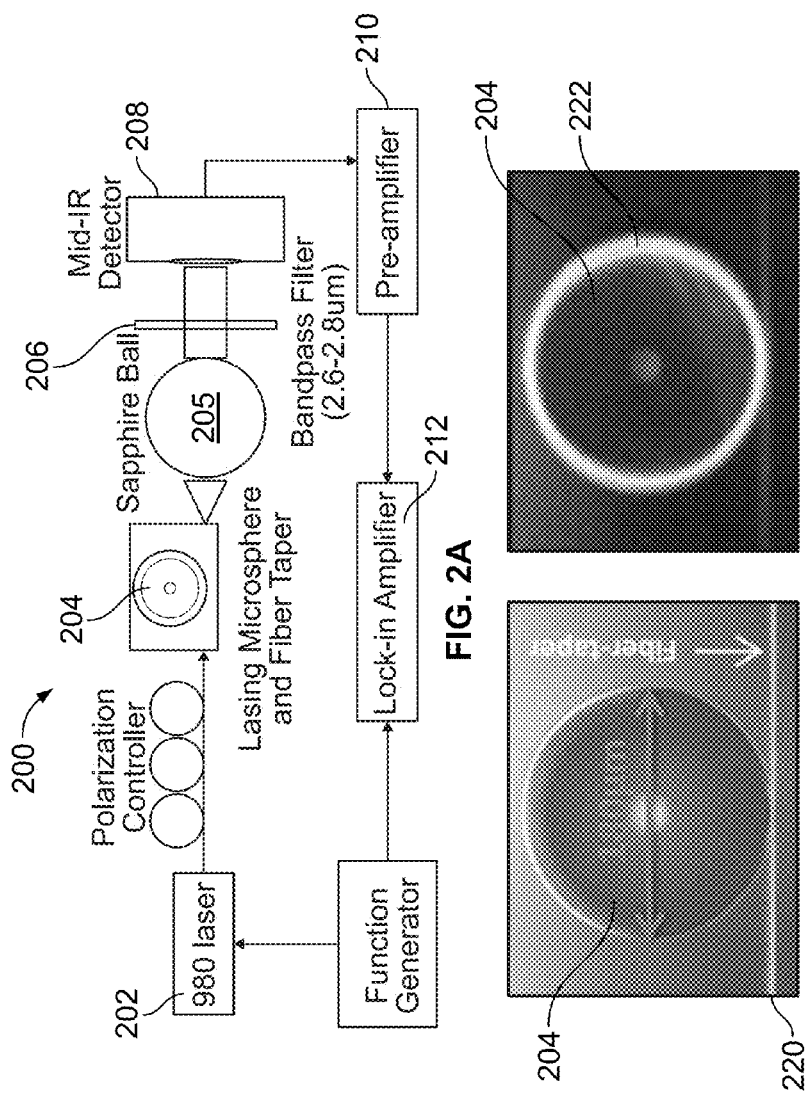

FIG. 2a is a schematic diagram of a setup of one embodiment of a mid-IR microlaser 200 of the present invention. A fiber taper coupling scheme may be used to both "incouple" the 980 nm pump power as well as to "outcouple" the mid-IR emission from the microsphere. The approximately 1 µm diameter fiber taper was fabricated from a low-OH multimode fiber (core size=50 µm) with relatively low transmission loss at the lasing wavelength (<0.1 dB/cm). Pump power may be provided by a single-mode FBG-line-narrowed laser diode 202 with a wavelength of 980 nm and a linewidth of less than 0.01 nm. A sapphire ball lens 205 may be used to collimate the optical power exiting the fiber taper. The collimated beam was filtered by a mid-IR bandpass optical filter 206 (with a center wavelength of 2.7 µm and a bandwidth of 200 nm to remove the transmitted 980 nm pump power and the optical radiation emitted by the Er:ZBLAN microsphere at other wavelengths (i.e., 540 nm, 1550 nm).

The mid-IR radiation was detected by a liquid nitrogen-cooled InSb MIR detector 208. To improve the signal-to-noise ratio of the observed signal, the photocurrent was amplified by a transimpedance amplifier 210 and measured using a lock-in amplifier 212. FIG. 2b shows a micrograph of the top-view of the microsphere 204 coupled to fiber taper 220.

Based on the measured value of the quality factor at 1.5 µm, a Q of >$10^7$ may be obtained for an undoped ZBLAN microsphere in the 2.5-3.8 µm wavelength range. Assuming a minimal increase in scattering losses, since there is negligible anticipated Er ion (excited state) absorption in this wavelength range, the Q of the Er-doped microspheres is comparable (>$10^6$) at these MIR wavelengths. Emission 222 is a known upconversion fluorescence from the $^2H_{11/2}$ and $^4S_{3/2}$ levels to the ground state of erbium ions. The confinement of emission 222 to the equatorial plane near the micro-sphere surface provided a strong visual verification of the coupling of the 980 nm pump to the WGMs.

Figure 3:
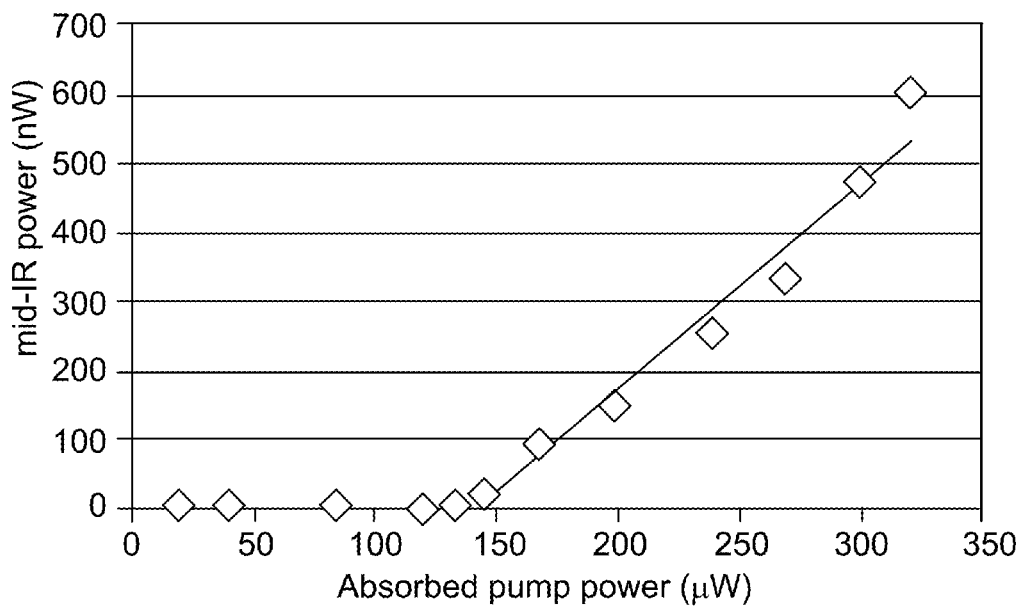
FIG. 3 shows measured mid-IR laser output power plotted against absorbed pump power for the microspherical laser shown in FIG. 2b. The absorbed pump power is the difference between the transmitted pump powers in the presence and absence of the Er:ZBLAN microsphere.

FIG. 3 shows the measured mid-IR laser output power plotted versus the pump power absorbed and scattered by microsphere 204. The absorbed pump power shown is the difference between the transmitted pump power in the presence and absence of the microsphere and, therefore, includes both contributions of absorbed and scattered powers.

Since the same fiber taper was used to couple in the 980 nm pump power and to couple out the 2.7 µm mid-IR laser power, simultaneous phase matching was not possible, and the use of two couplers such as two fiber tapers on opposite sides of the microsphere would be preferable in other embodiments. The threshold pump power is estimated to be 150 µW by extrapolation of the linear lasing region. The estimated slope efficiency is 0.35%. During these measurements, the microsphere was kept in continuous contact with the fiber taper to reduce the power variations due to coupling gap instabilities; however, the mid-IR power also appeared to have a maximum value at this close contact (zero gap) position (indicating that the fiber taper is not thin enough, and that the 980 nm pump radiation was still undercoupled even when the taper is in close contact). Varying the distance of these coupling gaps would be preferable in other embodiments of this invention.

In another embodiment, optimized coupling using a single mode fiber taper and a tunable narrow linewidth 980 pump laser may be used to improve the slope efficiency while reducing the threshold power. In addition, the larger threshold power, compared with the previous results reported for visible and near-IR WGM microlasers, are attributable to the relatively low gains that are inevitable at lower pump intensities when significant cross-relaxation via ETU processes are not yet possible (because of the relatively low populations in these excited states at threshold pump powers). The use of higher pump powers are preferable in alternate embodiments.

Figure 4:
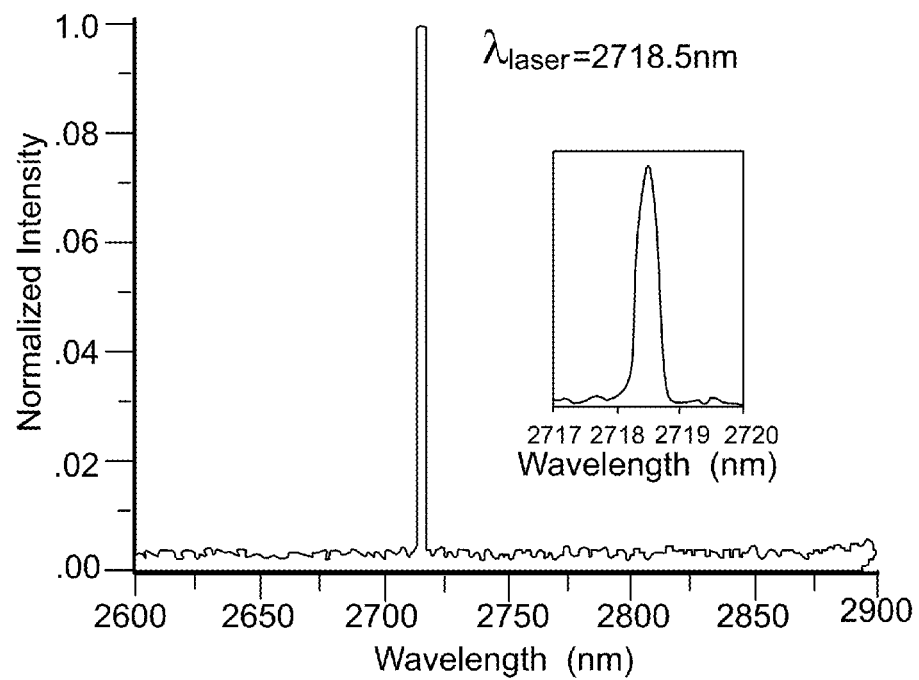
FIG. 4 shows the measured output spectrum of the mid-IR emission from the Er:ZBLAN microspherical laser at an absorbed pump power of 300 μW.

FIG. 4 shows the measured spectrum with a peak wavelength of approximately 2718.5 nm, which is consistent with the results reported for Er:ZBLAN fiber lasers.

Additionally, in other embodiments, the output power may become oscillatory due to thermo-optomechanical coupling. For passive ZBLAN microspheres pumped in the near-IR regime, these oscillations can translate quality factor degradation and resonant wavelength shifts to variations of oscillation frequency. As such, the frequency of the self-excited mid-IR thermo-optomechanical oscillator will be sensitive to the concentration of molecules with absorption lines near the laser wavelength.

Figure 5:
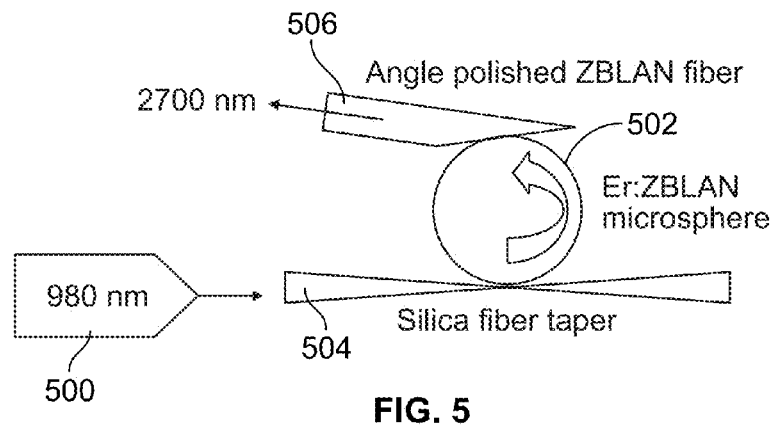
FIG. 5 is a schematic diagram of the configuration for another embodiment of an MIR microspherical laser of the present invention.
Figure 6:
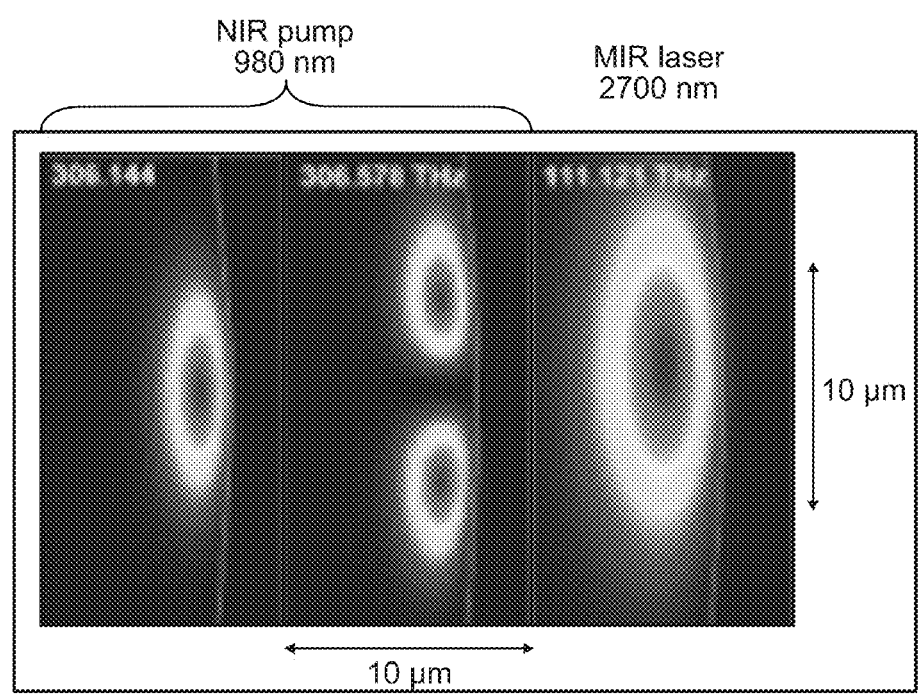
FIG. 6 shows numerical calculations for WGM mode distribution for the fundamental WGM at 2700 nm and 980 nm as well as the second order azimuthal mode at 980 nm.

As shown in FIG. 5, laser 500 provides a wavelength of 980 nm and is coupled to microsphere 502 by silica fiber taper 504. Microsphere 502 is fabricated using a uniformly doped (8 mol. %) Er:ZBLAN fiber. Microsphere 502 has a wavelength of 2.7 µm as its optical transmission, which is transmitted by angled, polished ZBLAN fiber 506. As shown in FIG. 6, the overlap between the pumped region and the fundamental WGM (at 2700 nm) is controllable by adjusting the pump laser wavelength to contain an appropriate admixture of modes, a feature that enables highly efficient modal overlap.

Figure 7:
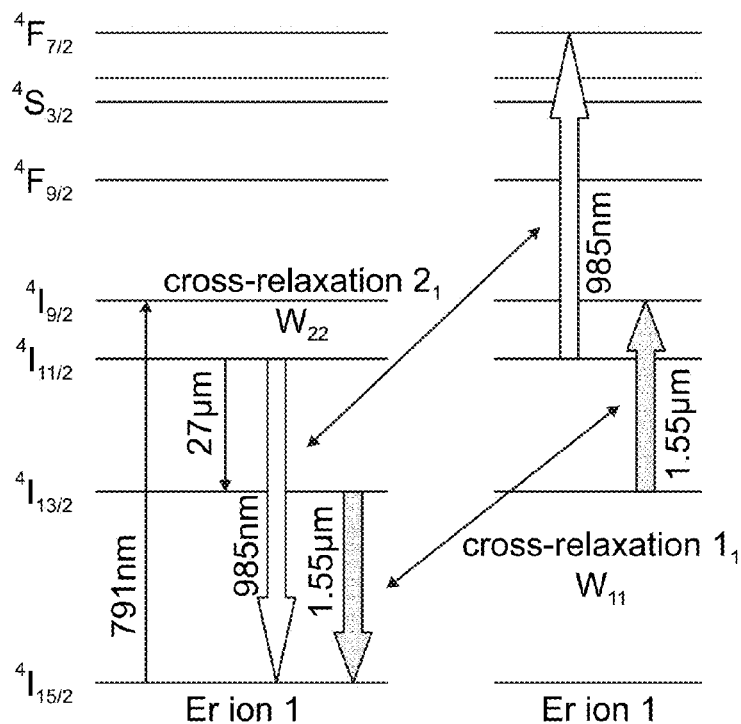
FIG. 7 is a partial energy level diagram of $Er^{3+}$ ions in ZBLAN depicting dominant cross relaxation processes.
Figure 8:
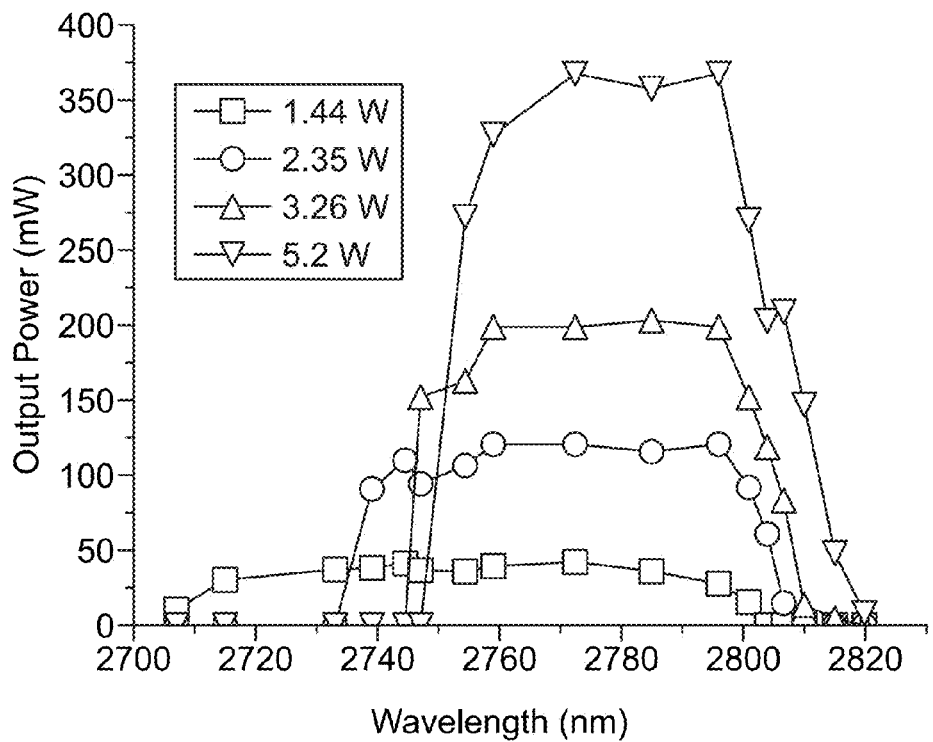
FIG. 8 shows tuning curves for diode-pumped Er:ZBLAN fiber lasers at low pump powers.

FIG. 7 shows the energy level diagram of Er:ZBLAN, and schematically depicts the removal of the population bottleneck for the 2700 nm transition (caused by the shorter lifetime of the $^4I_{11/2}$ upper laser level) by the use of cross-relaxation processes in (via dipole-dipole interactions and heavy doping, up to 100,000 ppm). Relatively efficient MIR laser action has been demonstrated in highly relevant spectral regions (2.7-3.5 um) in Er:ZBLAN, and wide tuning (~120 nm) of the 2700 nm $^4I_{11/2}$ to $^4I_{13/2}$ transition has also been demonstrated as shown in FIG. 8.

Using the fabrication method of the present invention, and the principles developed in the context of MIR fiber lasers, lasing near the 2.7 micron transition in Er:ZBLAN in mid-IR microresonator-based lasers is achieved. When sufficient pump power (at 980 nm) is coupled to a uniformly doped Er:ZBLAN microresonator, the combination of the population inversion (between the $^4I_{11/2}$ and $^4I_{13/2}$ states) and high-Q MIR resonance results in low-threshold laser action near 2700 nm with extremely narrow linewidths.

Figure 9:
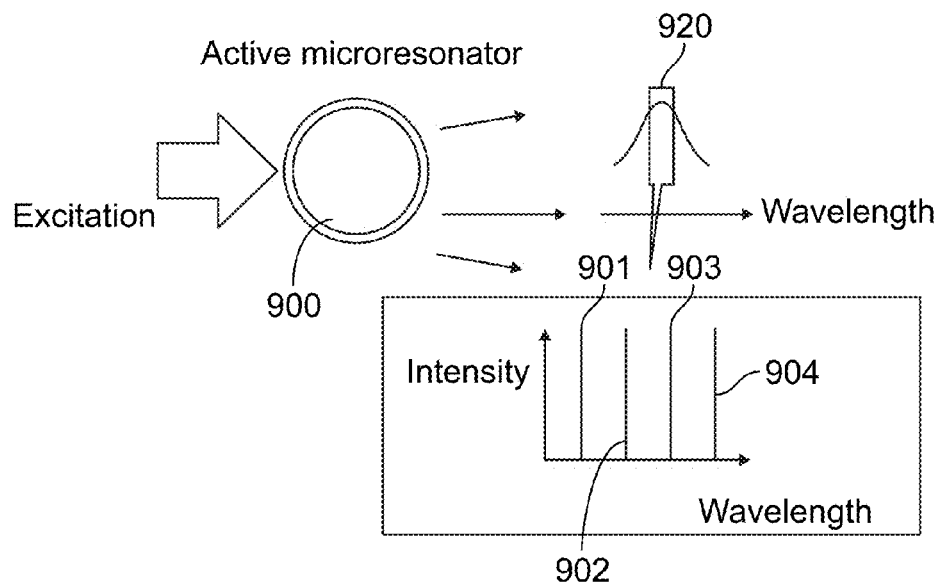
FIG. 9 shows the resonant luminescent source and its structured spectrum.

In another embodiment, the present invention provides a microresonator that utilizes the interaction between the evanescent field of a resonant optical source and the gas molecules. The optical source 900 may be an active high-Q optical microresonator with a structured emission spectrum consisting of nearly-equally spaced narrow lines 901-904, as well as sensing unit or detector 920 as shown in FIG. 9.

Active microresonator 900 is excited by an optical beam (excitation) from a microlaser as described above, another type of laser, or another source. Depending on the level of excitation of microresonator 900 may operate below lasing threshold (where the linewidth of the emission lines is limited by the quality factor of the cavity) or above lasing threshold (where the linewidth of the emission lines is limited by spontaneous emission). Near the central frequency ($v_0$) of a molecular absorption line, the collective polarization of gas molecules manifests itself as a complex refractive index featuring rapid and large variations in both the real and imaginary parts.

Figure 10:
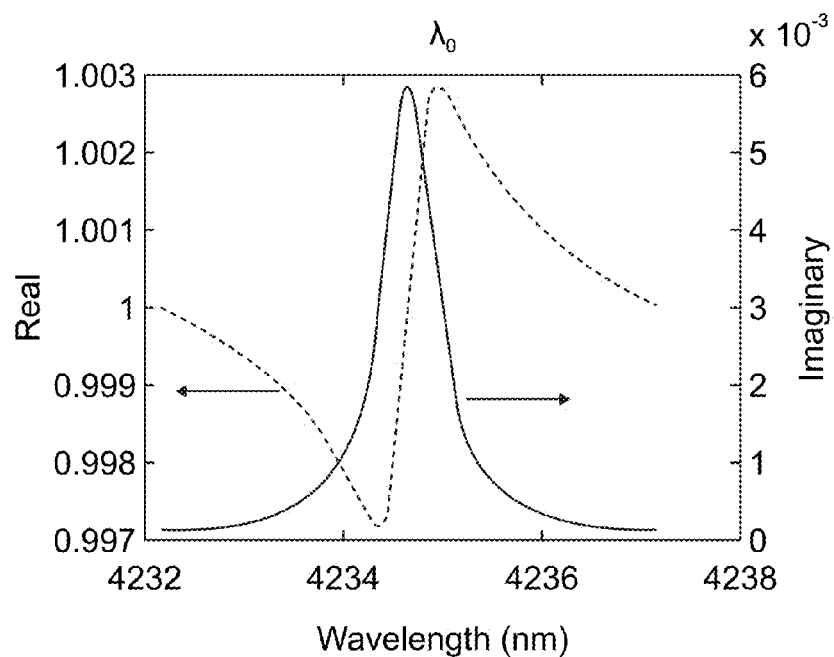
FIG. 10 shows a spectra of real and imaginary parts of refractive index of pure $CO_2$ at atmospheric pressure in the vicinity of the strongest absorption resonance.

FIG. 10 illustrates the variation of the real and imaginary parts of the refractive index for the case of a $CO_2$ molecule near the absorption/emission line centered at 4235 nm.

When molecules interact with the high-Q luminescent/lasing microresonator (through the evanescent optical field), the real part of the molecular refractive index changes the effective index of the corresponding optical modes while the imaginary part degrades their quality factor.

As a result, the resonances with wavelengths shorter than $\lambda_0 = c/v_0$ shift to lower wavelengths while those with wavelengths longer than $\lambda_0$ move to even longer wavelengths. Such a bi-directional wavelength shift due to the rapid variation in the dispersion near the molecular absorption peak increases the non-uniformity of the mode spacing near $\lambda_0$, while the quality factor degradation broadens the linewidth and changes the coupling strengths of the modes.

FIG. 11 shows the transmission spectrum of the resonator in the absence and presence of gas molecules. At the absorption spectrum of the target molecule, the change in the nearest, adjacent line pair shows the most pronounced changes which diminish with each successive line pair. Specifically, center line 1108, which is at or near the maximum absorption line strength of the target molecule, has on either side line pairs: 1110A and 1110B; 1120A and 1120B; 1130A and 1130B; 1140A and 1140B and 1150A and 1150B. For line pair 1110A and 1110B, the presence of the target molecule results in a decrease in height, a broadening of the line and increased distance from center line 1108. As shown, for each successive line pair, this change is diminished.

Although Whispering-Gallery mode (WGM) microlasers and luminescent sources are the best choices for the implementation of the present invention (due to their compact size and large quality factor), all other high-Q resonant sources with at least two modes near the molecular absorption region, can also be used. Since the strongest absorption lines of the important gas molecules are usually in the mid-IR spectral region, the present invention is much more effective when the optical emission is in the mid-IR spectral range (for example the mid-IR emission from Erbium doped ZBLAN microspheres). In other embodiments, the wavelength of the resonant source is approximately matched to the molecular absorption region of one or more molecules to be detected.

FIG. 12 schematically depicts the emission spectrum of a small microresonator-based luminescent or laser source. Specifically, FIG. 12a shows the impact of molecular absorption on transmission spectrum of a microresonator where lines 1202 and 1203 are the refractive indices of the microresonator and the surrounding medium, respectively. $\Delta\lambda$ is resonant wavelength shift and dM is the change of the transmission dip depth. FIG. 12b shows the spectra of real and imaginary parts of refractive index of pure $CO_2$ at atmospheric pressure in the vicinity of the strongest absorption resonance.

A band-pass optical filter is used to select two resonant lines (from the comb-like emission spectrum) within the absorption bandwidth of the target molecule. Alternatively, the source naturally emits only two lines. In other embodiments, the source emits a plurality of lines that are nearly identical in wavelength and spacing.

When interacting with the gas molecules, the two lines or line pair 1202 and 1203 move in opposite directions thereby increasing the distance between the two as shown by arrows 1212 and 1214. In addition, the changed lines 1220 and 1221, become broader and smaller in height. One or more of these changes may be monitored in the RF domain by detecting the emission in a photodetector 1200 and feeding the photocurrent to an RF frequency monitoring device (e.g. RF spectrum analyzer).

As shown in FIG. 12b, upon detection the emission lines mix and generate an RF signal with a frequency $f_{RF}=(v_1-v_2)=c/\lambda_2-c/\lambda_1 \approx c(\lambda_1-\lambda_2)/\lambda_1^2$. As such, changes in the spectral shift between the two wavelengths manifest itself via a shift in the detected RF frequency ($\Delta f_{RF}$), providing a relatively simple and novel method for trace sensing of numerous molecular species relevant to industrial, biological, and environmental sensing.

Figure 13A:
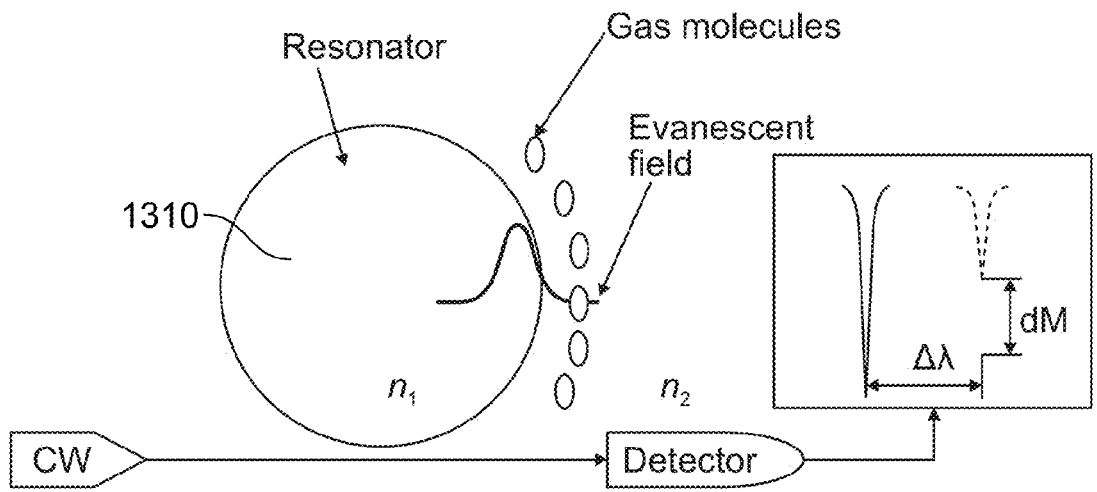
FIG. 13a shows a schematic configuration showing the impact of molecular absorption on transmission spectrum of a microresonator where $n_1$ and $n_2$ are the refractive indices of the microresonator and the surrounding medium, respectively. Δλ is resonant wavelength shift and dM is the change of the transmission dip depth.
Figure 13B:
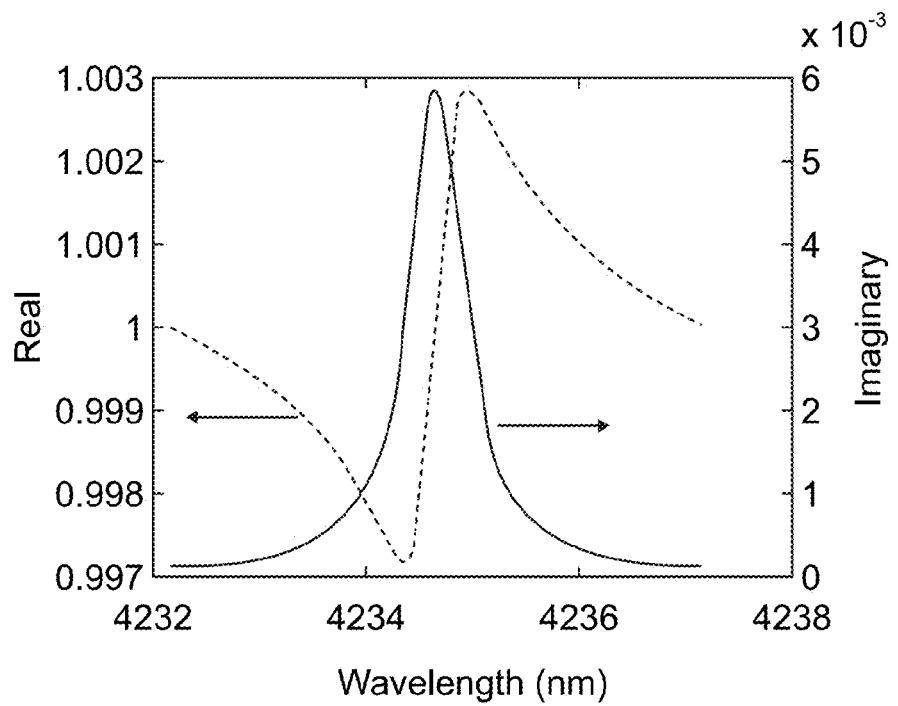
FIG. 13b shows a spectra of real (line 1300) and imaginary (line 1302) parts of refractive index of pure $CO_2$ at atmospheric pressure in the vicinity of the strongest absorption resonance.

A shown in FIGS. 13a and 13b, in another embodiment, the present invention provides a microcavity 1310 coupled to a tapered fiber. When a tunable laser light is transmitted through the fiber, the transmitted power can be written as, $$P_t = \frac{a^2 + |t|^2 - 2a|t|\cos\theta}{1 + a^2|t|^2 - 2a|t|\cos\theta}$$

where a is the field loss coefficient of the cavity, $\theta=2\pi R n_{eff}/\lambda$ designates the phase shift per circulation, and t represents the coupling losses at the resonator/fiber taper coupling region. $\lambda$ is the wavelength of input laser. The total effective loss coefficient at for propagating mode is related to a through $a=\exp(-\pi R\alpha t)$. The total loss depends on the intrinsic loss of the cavity due to material absorption and the absorption of the gas molecules through, $$\alpha_t = \alpha_i + \Gamma \alpha_g$$

where $\alpha_i$ is the intrinsic cavity loss and $\Gamma\alpha_g$ denotes the absorption from the gas molecules ($\Gamma$: is the ratio of the energy in the evanescent field and the circulating energy inside the cavity). The spectrum of $P_t$ consists of a series of Lorenzian shaped dips with resonant wavelength $\lambda_r$, is defined by, $$m\lambda_r = 2\pi R n_{eff}$$

where $n_{eff}=n_1+\Gamma n_2$ is the effective index of refraction of the circulating mode. $n_1$ and $n_2$ represent the refractive indices of dielectric microcavity and the surrounding environment, respectively. The resonance shift $\Delta\lambda$ associated with the change of $\Delta n_{gas}$ can be written as:

$$\frac{\Delta\lambda}{\lambda_r} \cong \frac{\Gamma\Delta n_{gas}}{n_{eff}}$$

The linewidth of the resonant dips ($\delta\lambda=\lambda/Q_{tot}$) limits the resolution for measuring $\Delta\lambda$, therefore $\Delta\lambda/\delta\lambda$ quantifying the detection limit. For a dielectric microresonator with index of ~1.5 and the surrounding medium with an index ~1, $\Gamma$ is estimated to be 1% (varies from 1% to 5% depending on the size and type of the microresonator).

At a low gas concentration, $\Delta n_{gas}$ is much smaller than the cavity/surrounding index difference, and thus the mode distribution doesn't change ($\Gamma$ is constant). A possible approach for enhancing the sensitivity and the detection limit is monitoring the wavelength near absorption band of the corresponding molecule. Meanwhile, large absorption brings the quality factor degradation, resulting in decreasing of $\Delta\lambda_{res}/\delta\lambda$, as shown in FIGS. 13a-13b. Consequently, a sweet spot exist where $\Delta\lambda_{res}/\delta\lambda$ is maximized.

The dispersion of a gas molecule undergoes a local maximum and a minimum across the absorption line, as shown in FIG. 13b. To estimate the dispersion in the vicinity of the gas absorption resonance, the well-known Kramer-Kronig relations between the real ($n_r$) and imaginary part ($n_i$) of the refractive index is used, $$\Delta n_r(\omega) = \frac{1}{\pi}\int_{-\infty}^{+\infty}\frac{n_i(\omega')}{\omega'-\omega}d\omega'$$

$$n_i(\omega) = -\frac{1}{\pi}\int_{-\infty}^{+\infty}\frac{n_r(\omega')-1}{\omega'-\omega}d\omega'$$

Here $\Delta n_r(\omega)$ is the refractive index change (dispersion) compared to unit value. When the laser wavelength is in resonance ($\theta=2\pi R n_{eff}/\lambda=2\pi m$). The dip depth can be quantified as, $$M = \frac{4Q_{int}Q_{ext}}{(Q_{int}+Q_{ext})^2} = \frac{4K}{(1+K)^2}$$

where $K=Q_{int}/Q_{ext}=\kappa^2/2\pi R\alpha_t$. Here $Q_{ext}=4\pi^2 R n_{eff}/(\lambda\kappa^2)$, $Q_{int}=2\pi n_{eff}/\lambda\alpha_t$ and $\kappa$ is the coupling coefficient from the fiber taper to the cavity.

At a low gas concentration ($\Gamma\alpha_g \ll \alpha_i$), the absorption caused by the presence of gas induces a change in the dip depth according to:

$$\frac{dM}{M} \cong -\left(\frac{1-K}{1+K}\right)\frac{\Gamma}{\alpha_i}\Delta\alpha_g = -L_{eff}(\lambda)\Delta\alpha_g(\lambda)$$

Figure 14B:
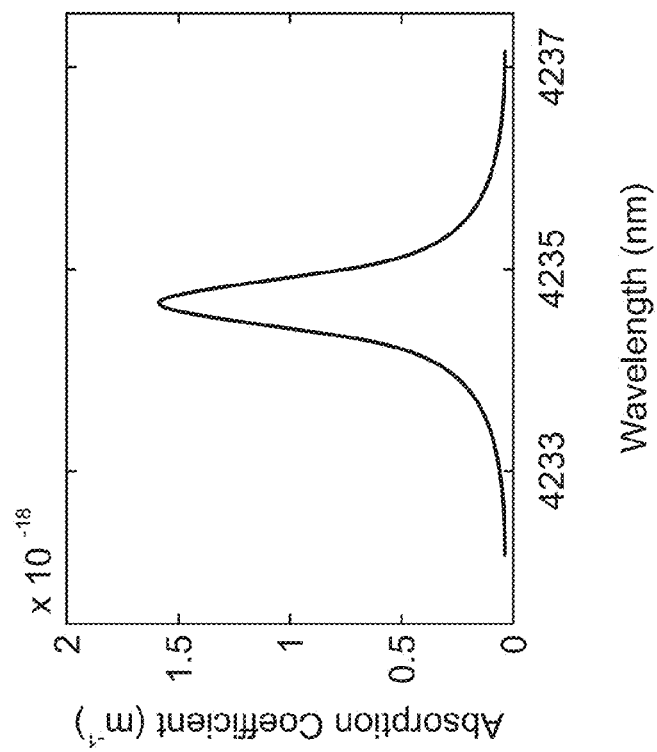
FIG. 14b shows a spectrum of the absorption coefficient of pure $CO_2$ at one atmosphere pressure and at room temperature.
Figure 14A:
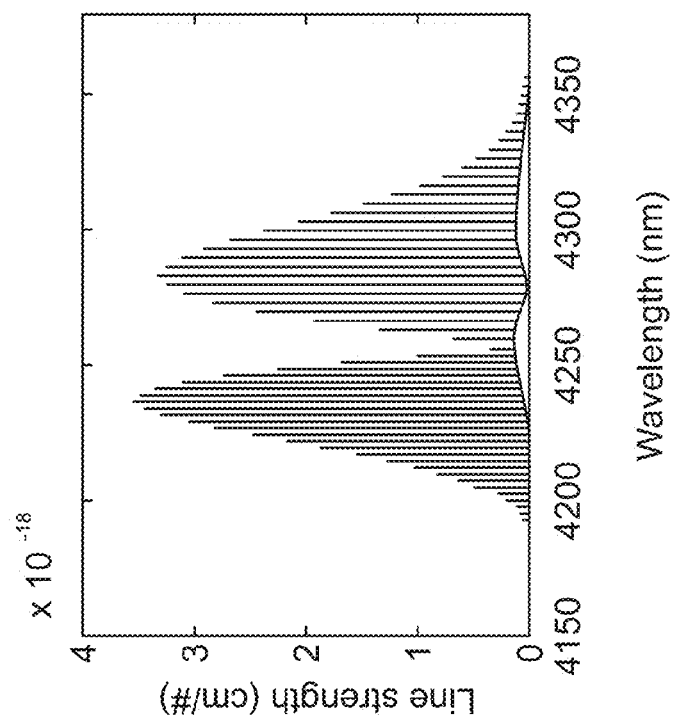
FIG. 14a shows a spectrum of the absorption line strength of $CO_2$ around the strongest absorption band.

In one embodiment, the interaction between the electromagnetic fields in a microresonator with $Q=5\times10^8$ ($\alpha_i=0.044$ m$^{-1}$) and carbon dioxide ($CO_2$) molecules in gas phase at room temperature was examined. $CO_2$ has a characteristically strong absorption band extending from 4.2 to 4.5 μm with strong peaks present at 4.23 and 4.28 μm. In this embodiment, it was determined to probe the absorption line of $CO_2$, centered at 4234.66 nm where the absorption line strength is strongest. The absorption spectrum of $CO_2$, obtained from the HITRAN 2008 database is shown in FIG. 14a. The absorption coefficient $\alpha_g$ is related to the absorption line strength S, and total number of molecules of absorbing gas per unit volume N through:

$$\alpha(v) = S \cdot g(v) \cdot N$$

where S (cm/#) is extracted from the HITRAN database as shown in FIG. 14a and g(v) is the Lorenz function to approximate the absorption line shape, which is written as, $$g(v) = \frac{\gamma}{(v-v_0)^2+\gamma^2}$$

where v is wavenumber in unit of cm$^{-1}$, $v_0$ is the resonant wavenumber and $\gamma$ is the broadening parameter including the air-broadening and self-broadening effects ($v_0$ and $\gamma$ can be extracted from HITRAN database). FIG. 14b shows the spectrum of absorption coefficient for the strongest line (4234.66 nm) at one atmosphere pressure and room temperature.

Figure 15A:
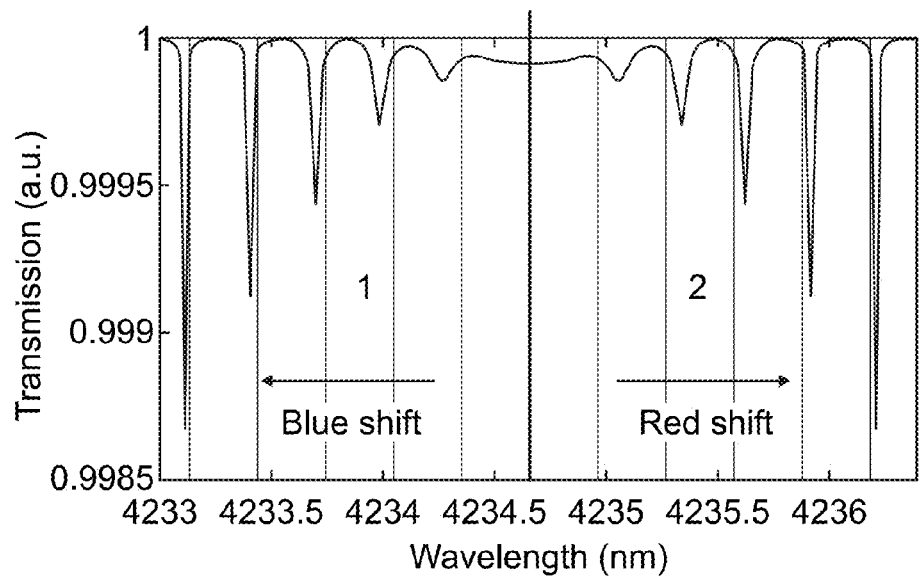
FIG. 15a shows a WGM transmission spectra showing the change between the resonant modes in absence of gas molecules (curves 1500) and in presence of gas molecules at one atmosphere pressure (curves 1502) in an undercoupled regime ($Q_{ext}=1\times10^9$).

In FIG. 15a, lines 1500 and 1502 show the locations of the transmission dips in the absence of gas molecules. Line 1504, which is located at the center of absorption peak, divides the spectrum into two areas, area 1 and 2. The presence of the gas molecules changes the effective index of the resonant modes. Thus in area 1 and 2, the resonant wavelengths shift to the left (blue shift) and right (red shift) relative to the absorption resonance peak, respectively. The optical resonant modes inside the gas resonance line shape are broadened due to absorption. This effect is significant when the resonant mode is closer to the absorption peak. At a certain wavelength, the dips completely disappear.

Figure 15B:
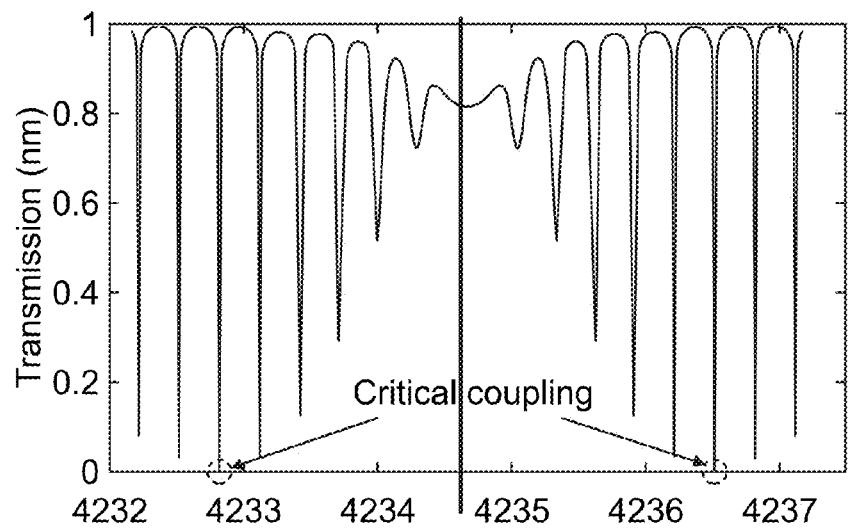
FIG. 15b shows what is shown in FIG. 15a in an overcoupled regime ($Q_{ext}=5\times10^5$).

In the undercoupled regime ($Q_{int}<Q_{ext}$), when the gas molecules interact with the WGMs, the decreasing of $Q_{int}$ leads to a reduction of dip depth. Meanwhile, the presence of gas molecules brings out the change of effective index, which induces the shift of resonant modes. FIG. 15b shows the case of overcoupled regime ($Q_{int}>Q_{ext}$). The only difference from the undercoupled is that degrading $Q_{int}$ might be equal to $Q_{ext}$ (critical coupling) at some wavelength, which leads to the largest dip depth (M=1, critical coupling). The gas absorption modulates the dip depth from the overcoupled regime ($Q_{int}>Q_{ext}$) to undercoupled regime ($Q_{int}>Q_{ext}$) in the wavelength domain. Note that this phenomenon happens only when the initial $Q_{int}$ is smaller than $Q_{ext}$ and gas concentration is large enough.

Figure 16A:
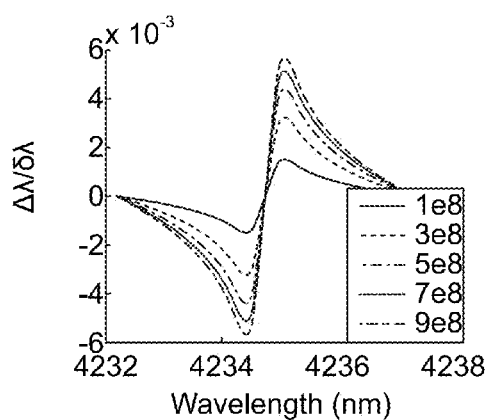
FIG. 16a shows spectra of Δλ/δλ at a gas concentration of 1 ppm for different values of $Q_{ext}$: $1\times10^8$, $3\times10^8$, $5\times10^8$, $7\times10^8$, and $9\times10^8$. Δλ and δλ are resonant wavelength shift and the linewidth of the loaded optical cavity, respectively.
Figure 16B:
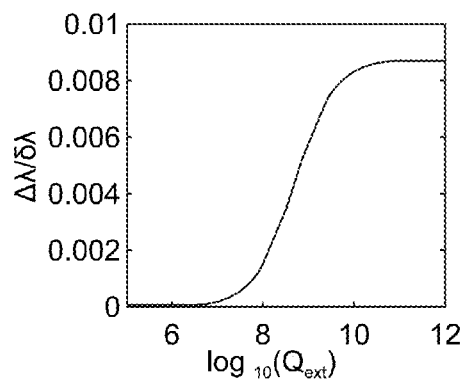
FIG. 16b shows ultimate detection limit plotted against $\log_{10}(Q_{ext})$. The gas concentration is 1 ppm.
Figure 16C:
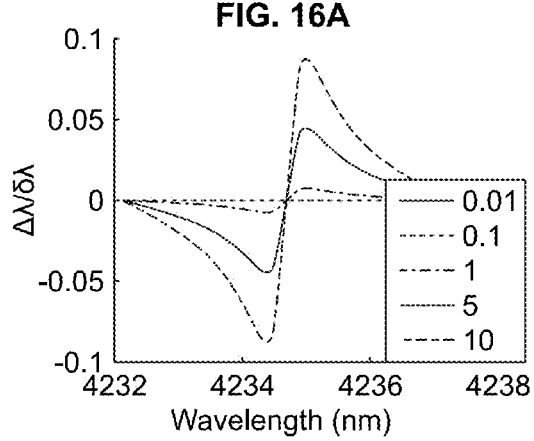
FIG. 16c shows spectra of detection limit Δλ/δλ for different gas concentration: 0.01, 0.1, 1, 5, 10 ppm. $Q_{ext}=1\times10^{10}$ (strongly undercoupled).
Figure 16D:
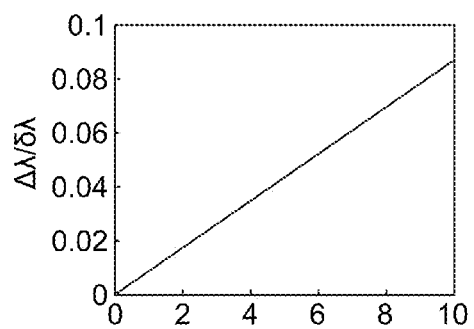
FIG. 16d shows ultimate detection limit Δλ/δλ plotted against gas concentration. $Q_{ext}=1\times10^{10}$.

Typically, the resonant wavelength shift is employed as the sensing parameter. Combining Eq. (2) and $Q_{tot}=\lambda_r/\delta\lambda$, $\Delta\lambda/\delta\lambda$ can be written as, $$\frac{\Delta\lambda}{\delta\lambda} = \frac{\Gamma \Delta n_{gas}}{n_{eff}} Q_{tot}$$

where $\delta\lambda$ is the linewidth of optical resonator mode. FIG. 16a shows the spectra of $\Delta\lambda/\delta\lambda$ at a gas concentration of 1 ppm for different values of $Q_{ext}$. $Q_{int}$ is fixed at $5\times10^8$. FIG. 16b shows $\Delta\lambda/\delta\lambda$ plotted against $Q_{ext}$. In the strongly overcoupled region ($Q_{ext}<<Q_{int}$, $Q_{ext}\sim Q_{tot}$), the broaden linewidth results in small $\Delta\lambda/\delta\lambda$ while in the strongly undercoupled regime ($Q_{ext}>>Q_{int}$, $Q_{int}\sim Q_{tot}$), $\Delta\lambda/\delta\lambda$ is constant because $Q_{int}$ undergoes a little change at low gas concentration. FIG. 16c represents the spectra of $\Delta\lambda/\delta\lambda$ for different gas concentrations (where $Q_{ext}=1\times10^{10}$). FIG. 16d denotes $\Delta\lambda/\delta\lambda$ plotted against the gas concentration in the strong undercoupled regime. Typically a $\Delta\lambda/\delta\lambda$ of 1% is detectable; so the ultimate limit of detection for $CO_2$ by monitoring relative resonance shift is $0.01\times n_{eff}/(\Gamma\Delta n_g(1\text{ ppm})Q_{int})=1.145$ ppm, which can be obtained in strongly undercoupled regime ($Q_{int}\sim Q_{tot}$).

Figure 17A:
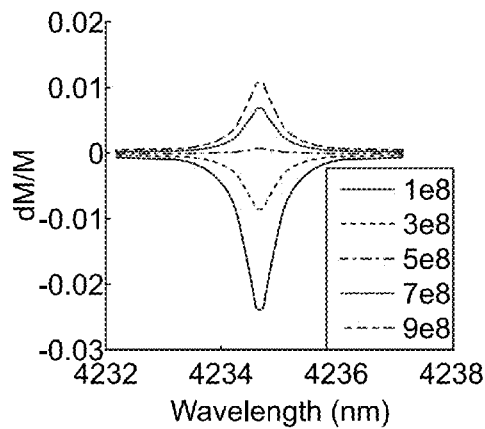
FIG. 17a shows spectra of relative dip depth changes at a gas concentration of a ppm and for different values of al $Q_{ext}$: $1\times10^8$, $3\times10^8$, $5\times10^8$, $7\times10^8$, and $9\times10^8$.
Figure 17B:
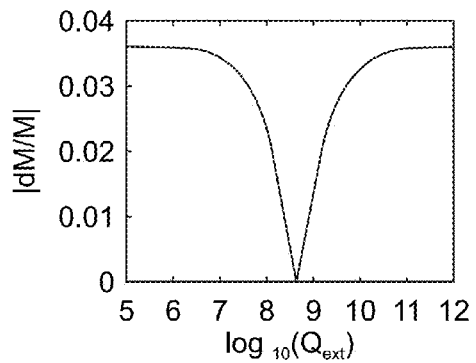
FIG. 17b illustrates the detection sensitivity via relative dip depth changes plotted against $Q_{ext}$ for the gas concentration of 1 ppm.
Figure 17C:
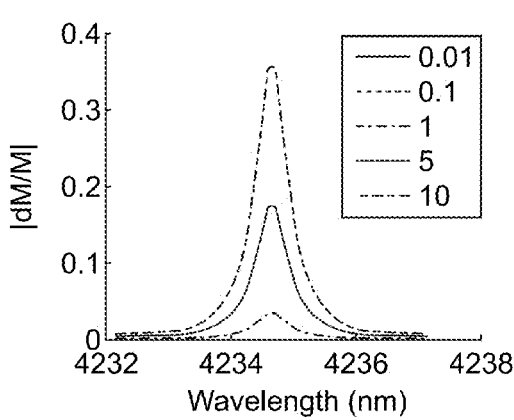
FIG. 17c shows spectra of relative dip depth changes at different gas concentrations: 0.01, 0.11, 5, 10 ppm. $Q_{ext}=1\times10^{10}$ (strongly undercoupled).
Figure 17D:
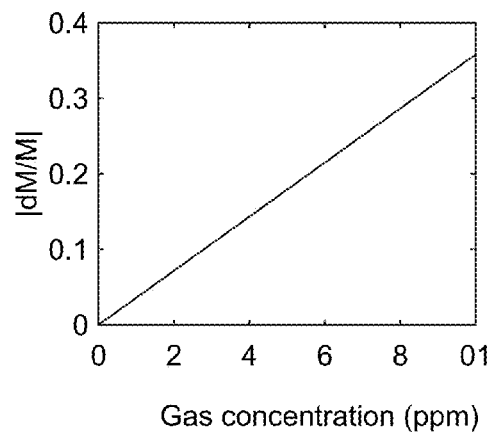
FIG. 17d shows the relative dip depth changes plotted against the gas concentration. $Q_{ext}=1\times10^{10}$.

The concentration of gas molecules can also be derived by monitoring the relative changes of transmission dip depth (dM/M). FIG. 17a shows the spectra of dM/M at a gas concentration of 1 ppm and for different values of $Q_{ext}$. $Q_{int}$ is fixed at $5\times10^8$. The sign of dM/M indicates whether the system is in the undercoupled (dM/M>0) or overcoupled (dM/M<0) regime. Assuming that 1% of |dM/M| is detectable, the ultimate detection limit for $CO_2$ is $0.01\times\alpha_r/(\Gamma\Delta\alpha_g(1\text{ ppm}))=0.276$ ppm=276 ppb (parts-per-billion), which is obtained in strongly undercoupled or overcoupled regime (|(1−K)/(1+K)|~1) and at the gas absorption resonance.

Figure 18:
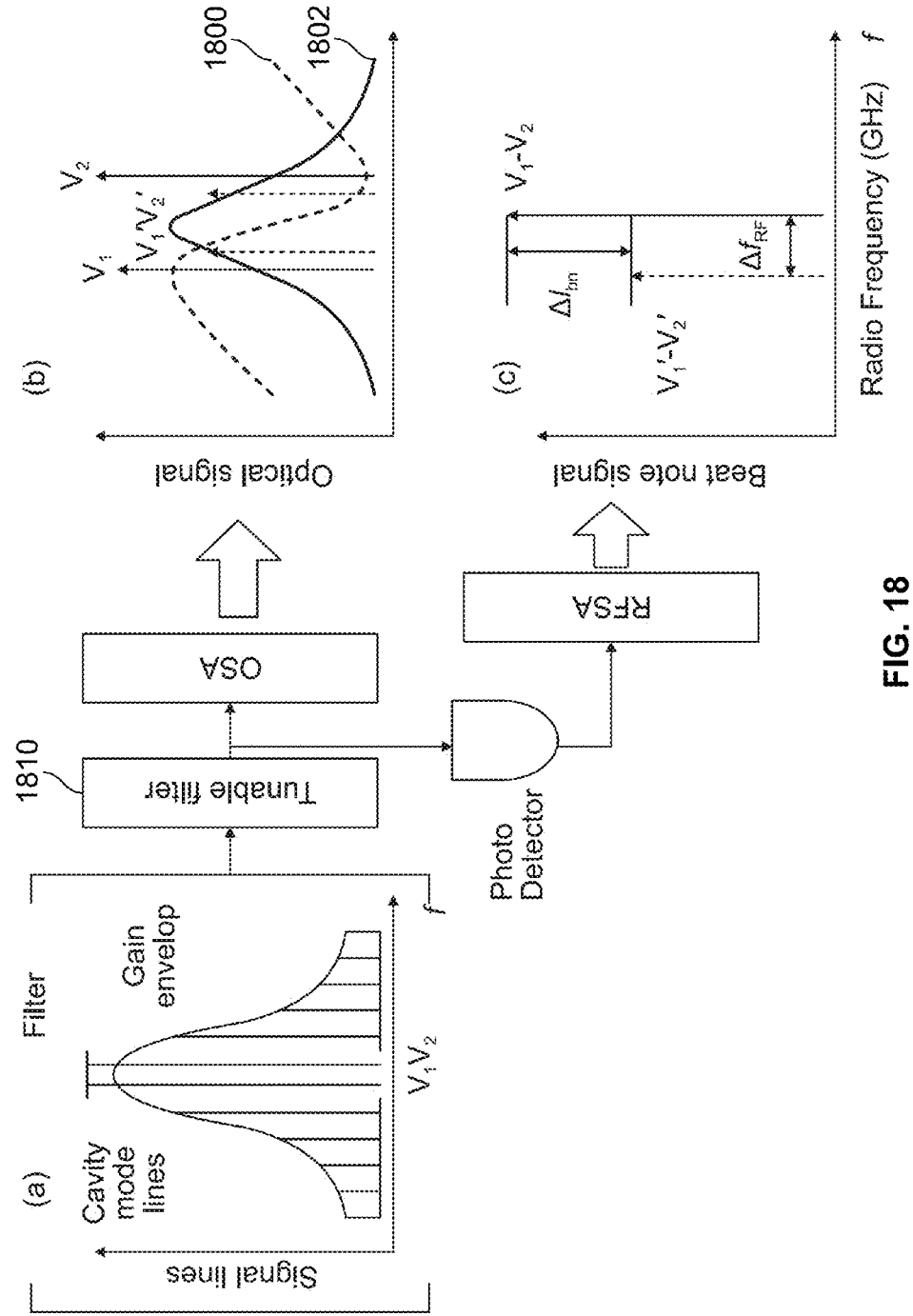
FIG. 18 shows laser lines, which are generated from a Mid-IR transparency cavity which have been filtered to leave two adjacent lines, whose frequencies are $v_1$, $v_2$. OSA: optical spectrum analyzer. RFSA: radio frequency spectrum analyzer. (b) In OSA, the laser frequency lines are shown with and without target molecules in optical frequency domain (THz) are different. Line 1800 is the real and line 1802 is the imaginary part of refractive index of the gas molecules. Dark solid and dashed lines are optical frequency lines with and without target gas molecules, respectively. $v_1$ and $v_2$ are the frequencies of the two laser lines without gas molecules. $v_1'$ and $v_2'$ are the frequencies of the two laser lines with gas molecules. (c) In RFSA, the beat note signal is seen at a radio frequency (RF) (GHz). Dark solid (without target gas molecules) and dashed lines (with target gas molecules) are the RF beat note signals of these two lines.

In addition to monitoring the aforementioned spectral changes (frequency shift and amplitude variations) directly, translation of such spectral interpretation caused by the surrounding gas molecules into the RF domain (GHz) is an alternative highly desirable and reliable method that may be used for use of very precise and accurate molecular sensing. As shown in FIG. 18, a tunable filter 1810 is used to remove all the laser lines other than the two successive ones, which are located at the maximum and minimum refractive index of the gas molecules. FIG. 18c shows the beat note frequency of two optical frequency lines with (solid lines) and without (dashed lines) target molecules. The presence of the target species leads to the variation of the amplitude and frequency of the beat note signal. The resulting beat note of these two laser lines produces a radio frequency (RF) signal that contains a direct mapping of the optical spectrum, including any absorption and phase shift imparted by the sample gas molecules.

In the various embodiments described above, the present invention provides a detection mechanism based on frequency shifts; this method is more reliable than one employing amplitude changes due to the fact that the amplitude is dependent of relative intensity noise (RIN) of the laser, and instability of the PZT controlling the coupling gap, which determines the ultimate optical Q. Moreover, if the two laser lines are tuned, for example, via thermal effects, in other embodiments, the present invention is able to identify the gas molecule among several mixed gases by observing the shift of RF signal, making this approach a potential method for directly probing molecules.

In other embodiment, the microresonators of the present invention use, but are not limited to, the above described microlasers. In addition, the present invention may use two adjacent laser lines, which are located in the local maximum and minimum target gas dispersion, to generate the RF beat note. Beating these two neighboring longitudinal modes requires increasing of the radius of the microresonator up to ~7 mm in which the evanescent field percent (F) decreases. Therefore the RF beat note of two adjacent azimuthal modes in a multimode microspherical laser is able to maintain the ultra-compact dimension of the microsphere while having relatively more evanescent field to interact with gas molecules and thereby decreases the detection limit.

While it is well known that the WGMs of different azimuthal mode orders in an ideal microsphere are degenerate, the fabricated microspheres are rarely perfectly spherical symmetric. This eccentricity is defined as e=(Rp−Re)/R, where Rp and Re are polar and equatorial radii respectively. The presence of eccentricity breaks the degeneracy of polar modes, leading to a frequency shift for the modes with the same radial and longitudinal modes number. Eccentric splitting between modes with successive azimuthal mode number is defined by:

$$\frac{\Delta v}{v_{nml}} = |v_{nml} - v_{n,m+1,l}| = -\frac{e}{6}\left(1 - \frac{3m^2}{l(l+1)}\right)$$

where n, m, l are radial, longitudinal and azimuthal mode numbers, respectively. The amplitude of each mode is dependent of the coupling between the fiber taper and the microsphere.

Figure 19:
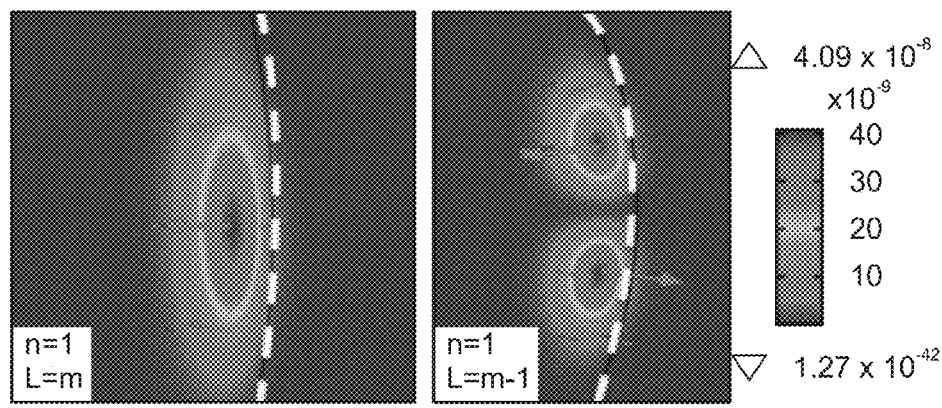
FIG. 19 provides numerical modeling of the electromagnetic intensity profile (V/m) of WGMs of a 15.257-μm-microsphere, with polarization of TM (COMSOL Multiphysics). The white dash lines are the boundary of the microsphere and the arrows denote the directions of the electric field.
Figure 20A:
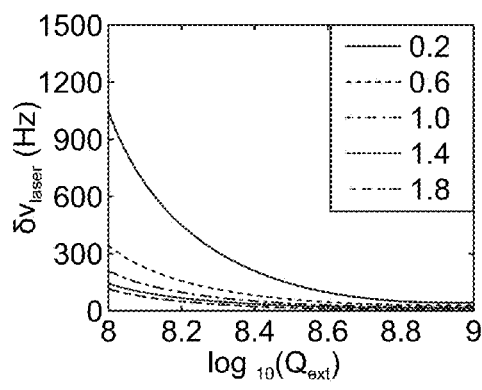
FIG. 20a shows the optical laser linewidth plotted against $\log_{10}(Q_{ext})$ for different output powers of 0.2, 0.6, 1.0, 1.4, and 1.8 μW.
Figure 20B:
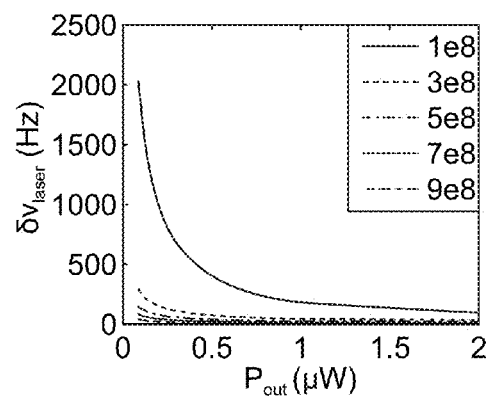
FIG. 20b shows the optical laser linewidth plotted against output power for different values of external Q: 1e8, 3e8, 5e8, 7e8 and 9e8.

In one embodiment, the radius of the eccentricity of the microsphere were chosen to be 15.257 μm and 0.428% such that the frequencies of the fundamental mode (|l−m|=0) and the adjacent azimuthal mode (|l−m|=1) are able to match the locations of the maximum and minimum of the $CO_2$ dispersion at 2702.578 nm at which the Mid-IR microlaser is lasing. Two TM modes are employed since they have larger evanescent field than TE ones. The electromagnetic field distributions of these two successive TM modes are depicted in FIG. 19.

The optical signals are separated by the desired frequency $f_{RF}$, which is the resulting beat frequency of the two incident electric fields. When the incident electric field has components at two frequencies, the electric field can be given by, $$E = A_1 \cos(2\pi v_1 t) + A_2 \cos(2\pi v_2 t + \phi)$$

where $\phi$ is the relative phase offset of the second signal. $A_1$ and $A_2$ designate the amplitudes of these two optical components. t is time. The current in the photodiode is proportional to the incident electric field through, $$i(t) = \eta\{A_1^2 + A_2^2 + A_1A_2\cos[2\pi(v_1 - v_2)t - \varphi] +$$
$$A_1A_2\cos[2\pi(v_1 + v_2)t - \varphi] + A_1^2\cos[4\pi v_1 t] + A_2^2\cos[4\pi v_2 t + 2\varphi]\}$$

where $\eta$ is the photodiode responsivity. The first three items given by the above equation represent two signals at dc and one at the differenced frequency $f_{RF}=|v_1-v_2|$. The other signals are at optical frequencies which beyond the responding wavelength of RFSA.

From the analysis above, the sensitivity is limited by the linewidth of RF beat note (RBW), $\delta f_{RF}$. Since the exact RF beat note position is determined by the cavity resonances, its noise is principally dependent of the phase noise characteristics in optical domain of the cavity resonances and ultimately by the quantum noise of the lasing mode, namely the Schawlow-Townes linewidth.

That the two lasing lines share a common cavity enables the cancellation of any optical frequency fluctuations caused by the vibration or thermal drift of the cavity length when the two frequencies are differenced, so that the beat-frequency noise will only depends on the uncorrelated noise on each optical tone. RBW can be translated directly from the relative optical linewidth ($\delta v_{OPT}/v_{OPT}$), $$\delta f_{RF}/f_{RF} = \delta v_{OPT}/v_{OPT}$$

where $\delta v_{OPT}$ is the optical linewidth of the laser sources and $v_{OPT}$ is the optical frequency.

Below threshold power (spontaneous emission), relative optical linewidth $\delta v_{OPT}/v_{OPT}$ is determined by the intrinsic cavity loss ($\delta v_{OPT}/v_{OPT}=1/Q$). The dispersion of $CO_2$ molecules gives $v_{OPT}=110.05$ THz and $f_{RF}=|v_1-v_2|=10.315$ GHz. The $Q_{int}$ of 5e8 results in RWB of 20.63 Hz. On the other hand, the linewidth of the stimulated emission above the lasing threshold dramatically decreases because of the high coherence of the lasing light. The linewidth narrowing is consistent with lasing process and should continue until the system reaches the ultimate quantum-limited variance of the optical frequency due to spontaneous emission, which is known as the Schawlow-Townes limit, $$\delta v_{laser} = \frac{\pi \mu h v^3}{P_{out} Q_{tot} Q_{ext}} = \frac{\pi h v^3}{P_{out}} \frac{(1+K)K}{Q_{int}^2}$$

where $\mu$ is the spontaneous emission factor, which is around 600. v is the cavity lasing frequency. h is the Plank's constant, and $P_{out}$ represents the output power of the lasing cavity. The above equation indicates that $\Delta v_{laser}$ is inversely proportional to the output laser power $P_{out}$, intrinsic quality factor and external Q, which leads to the fact that the narrow linewidth happens in the strongly undercoupled regime.

For $Q_{ext}=1e9$ and $P_{out}=2$ μW, the laser linewidth from the cavity is estimated to be 2.56 Hz, resulting in RBW=0.24 mHz. However, the jitter of the laser lines and the resolution of the detection set the ultimate limitation of RBW and the stability of the RF beatnote. Stable RF beatnote with RBW of 10 mHz is reasonably achievable. Similar with the aforementioned analysis, 1 ppm $CO_2$ at 2701.578 nm induces the frequency shift of 63 Hz, which corresponds to the RF shift of 126 Hz. Assuming $\Delta f_{RF}/\delta f_{RF}=1$ is detectable, the present invention is able to readily obtain the minimum detectable absorption coefficient (MDA) of 2e-8 cm$^{-1}$, which corresponds to 79 part per trillion (ppt) of gas concentration detection limit (CDL). If a similar microlaser is able to be lasing around 4234 nm, where $CO_2$ has the maximum absorption line strength (around two orders of magnitude lager), the resulting CDL is improved two orders of magnitude.

In other embodiments, the present invention provides a gas detection system that takes advantage of the resonant molecular absorption induced effects on Mid-IR WGM spectra, based on the two existing sensing mechanism. The large gas absorption resonance and different dispersion behaviors across the absorption resonance enables the identification of the component of gases with relatively high detection sensitivity. By employing the method of monitoring the shift of RF beat note of two laser lines, a detection limit of 8 ppt level is attained in the strongly undercoupled regime, which allows the independence of sensitivity on technical noise. A further improvement of sensitivity can be achieved by increasing the interaction factor $\Gamma$. As a result, the embodiments of the present invention are able to function as optical gas sensors for identification of unclear gas with ultra-high sensitivity in a wide range of applications.

In yet another embodiment, the present invention provides an optical molecular sensing device, comprising an optical resonator adapted to be connected to an excitation source. The optical resonator has an emission spectrum comprised of a plurality of wavelengths whose individual emission bandwidths are much narrower than the spacing between any two adjacent wavelengths. In addition, a detection unit and a RF frequency counter to detect at least one RF beat note resulting from detecting the emission spectrum of the optical resonator may be used.

A target molecule is detected by a change in frequency of the RF beat note indicating the presence of a target molecule. In addition, the emission spectrum of the device may be within the absorption region of one or more target molecules and be comb-like, consisting of lines of nearly identical height and spacing.

A tunable filter may also be used to remove all lines of the emission spectrum other than two successive lines and where the absorption of the target molecule is within the two successive lines. The presence of the target molecule causes an increase in line spacing and line broadening. This change is detected by measuring the RF beat note between the two successive lines to indicate the presence of a target molecule.

In other embodiments, the excitation source may be a laser operating at a 2.7-2.8 um spectral range or another source that is capable of generating an optical output comprised of a plurality of wavelengths at narrowband emissions, such that these interact with at least one target molecule.

In other embodiments, the laser operates at a temperature greater than 0 degrees Celsius and may also include one or more Er:ZBLAN microspheres coupled to a 980 nm laser. The one or more Er:ZBLAN microspheres may be uniformly doped with Er densities of greater than 1 mole percent.

In other embodiments, the present invention provides a method of detecting the presence of a target molecule comprising the steps of monitoring at least one RF beat note resulting from detection of the optical output. Measuring a change in frequency of the RF beat note indicating the presence of a target molecule. In addition, the method may include the removal of all lines of the output other than two successive lines, with the absorption of the target molecule being within the two successive lines.

The change in the RF beat note may be generated by the interaction of target molecules and the optical field due to the asymmetric polarization response of the target molecule in the vicinity of its absorption line. An increase in line spacing and line broadening caused by the presence of the target molecule is then detected by measuring the RF beat note between the two successive lines.

In other embodiments of the invention, different mid-infrared host glasses such as chalcogenide, telluride, or other fluoride glasses may be used for the microresonators to be used in the present invention.

In other embodiments of this invention, different rare-earth (such as Dysprosium, Presodymium, Holmium and Terbium) and transition metal dopants (such as Fe) may be used individually or as plural co-dopants, preferably at high doping densities (above 0.5%) to result in mid-infrared light emitting sources at other wavelengths optimized for the sensing of other molecules such as moisture (water vapor), methane, nitrogen oxide, and hydrogen sulfide, as needed for appropriate applications such as healthcare monitoring, industrial process monitoring, and environmental monitoring.

While the foregoing written description enables one of ordinary skill to make and use what is considered presently to be the best mode thereof, those of ordinary skill will understand and appreciate the existence of variations, combinations, and equivalents of the specific embodiment, method, and examples herein. The disclosure should therefore not be limited by the above described embodiments, methods, and examples, but by all embodiments and methods within the scope and spirit of the disclosure.

What is claimed is:

1. An optical molecular sensing device, comprising:
   an optical resonator adapted to be connected to an excitation source;
   said optical resonator having an emission spectrum comprised of a plurality wavelengths in the mid-infrared; and
   a detection unit and a RF frequency counter adapted to detect an RF beat note frequency resulting from detecting the emission spectrum of said optical resonator in the absence of a target molecule and a change in frequency of said RF beat note resulting from the presence of the target molecule.

2. The device of claim 1 wherein said emission spectrum is within the absorption region of one or more target molecules.

3. The device of claim 1 wherein said emission spectrum is a comb-like emission spectrum.

4. The device of claim 3 wherein said comb-like emission spectrum consists of lines of nearly identical height and spacing.

5. The device of claim 1 further including a tunable filter to remove all lines of said emission spectrum other than two successive lines.

6. The device of claim 5 wherein the absorption of the target molecule is within the two successive lines.

7. The device of claim 1 wherein said change in said RF beat note results from an increase in line spacing and line broadening caused by the presence of the target molecule.

8. An optical molecular sensing device, comprising:
   an optical resonator adapted to be connected to an excitation source;
   said excitation source is a laser operating at a 2.7-2.8 um spectral range;
   said optical resonator having an emission spectrum comprised of a plurality wavelengths; and
   a detection unit and a RF frequency counter adapted to detect an RF beat note frequency resulting from detecting the emission spectrum of said optical resonator resonator in the absence of a target molecule and a change in frequency of said RF beat note resulting from the presence of the target molecule.

9. The device of claim 8 wherein laser operates at a temperature greater than 0 degrees Celsius.

10. The device of claim 8 wherein said laser includes one or more fluoride, telluride, or chalcogenide microspheres.

11. The device of claim 10 wherein said one or more microspheres are uniformly doped Er:ZBLAN at greater than 1 mole percent.

12. The device of claim 8 further including a tunable filter to remove all lines of said emission spectrum other than two successive lines.

13. The device of claim 8 wherein said change in said RF beat note results from an increase in line spacing and line broadening caused by the presence of the target molecule.

14. A method of detecting the presence of a target molecule comprising the steps of:
   generating an optical output from an optical source comprised of a plurality wavelengths from a source that allows interaction of the optical field with at least one target molecule;
   monitoring at least one RF beat note resulting from detection of the optical output in the absence of a target molecule; and
   measuring a change in frequency of said RF beat note indicating the presence of a target molecule.

15. The method of claim 14 further wherein all lines of said output are removed other than two successive lines, said absorption of the target molecule is within the two successive lines.

16. The method of claim 15 wherein an increase in line spacing and line broadening caused by the presence of the target molecule is detected by measuring the RF beat note between the two successive lines.

17. The method of claim 15 further including the step of exciting the optical source using a laser operating at a 2.7-2.8 um spectral range, at a temperature greater than 0 degrees Celsius, and wherein said laser includes one or more Er:ZBLAN, fluoride, telluride, or chalcogenide microspheres coupled to a 980 nm laser.

18. The method of claim 17 wherein said microspheres are doped with Erbium, Dysprosium, Presodymium, Holmiu, Terbium or transition metal dopants at high doping densities above 0.5 mole percent.

19. The method of claim 14 wherein the change in RF beat note is generated by the interaction of target molecules and the optical field due to the asymmetric polarization response of the target molecule in the vicinity of its absorption line.

* * * * *